United States Patent
Eveland et al.

(10) Patent No.: US 6,924,139 B2
(45) Date of Patent: Aug. 2, 2005

(54) SELF-CONTAINED BIOLOGICAL INDICATOR

(75) Inventors: Randal W. Eveland, Concord, OH (US); Tricia A. Cregger, Fairlawn, OH (US)

(73) Assignee: STERIS Inc., Temecula, CA (US)

( * ) Notice: Subject to any disclaimer, the term of this patent is extended or adjusted under 35 U.S.C. 154(b) by 114 days.

(21) Appl. No.: 10/620,824

(22) Filed: Jul. 16, 2003

(65) Prior Publication Data

US 2005/0014214 A1 Jan. 20, 2005

(51) Int. Cl.⁷ .............................................. C12M 1/34
(52) U.S. Cl. .............................. 435/287.4; 435/287.6; 435/287.7
(58) Field of Search .................. 422/58, 59; 435/287.4, 435/287.6, 287.7, 288.1

(56) References Cited

U.S. PATENT DOCUMENTS

| | | | |
|---|---|---|---|
| 4,914,034 A | 4/1990 | Welsh et al. ................ | 435/296 |
| 5,139,957 A | 8/1992 | Grack ......................... | 436/135 |
| 5,167,923 A | * 12/1992 | Van Iperen .................. | 422/58 |
| 5,516,648 A | 5/1996 | Malchesky et al. ........... | 435/31 |
| 5,736,355 A | 4/1998 | Dyke et al. .................... | 435/31 |
| 5,770,393 A | 6/1998 | Dalmasso et al. ............. | 435/31 |
| 5,801,010 A | 9/1998 | Falkowski et al. ............ | 435/31 |

* cited by examiner

Primary Examiner—David A. Redding
(74) Attorney, Agent, or Firm—Kusner & Jaffe; Michael A. Centanni

(57) ABSTRACT

A self-contained biological indicator for evaluating the effectiveness of a sterilizer utilizing an anti-microbial gas or liquid fluid. The indicator is comprised of a tubular casing having open ends and defining an interior chamber. A source of viable microorganisms is disposed within the chamber. A frangible ampoule containing a culture medium capable of promoting growth of the microorganism and a detector means capable of reaction with the metabolites of the microorganism to produce a visual indication is disposed within the chamber. The ampule is operable by pressure applied to an external surface thereof to permit the microorganism and the medium to come into contact with each other. A cap assembly is mounted to each end of the tubular casing. Each cap assembly includes a telescoping element movable from a first position defining an opening communicating with the chamber and a second position crushing the ampoule and forming a gas/fluid impermeable seal around the chamber.

10 Claims, 4 Drawing Sheets

SELF-CONTAINED BIOLOGICAL INDICATOR

FIELD OF THE INVENTION

The present invention relates to biological indicators for evaluating the efficacy of a sterilization process, and more particularly, to a self-contained biological indicator.

BACKGROUND OF THE INVENTION

Sterilization is a process conducted in a specially designed chamber or sterilizer that results in a complete eradication of all viable microorganisms. Sterilization techniques have evolved over time from the traditional methods employing saturated steam at elevated temperature and ethylene oxide gases to more modern techniques, such as those employing liquid, vapor and plasma. Regardless of the technique utilized, the effectiveness of the applied sterilization process must be evaluated especially when sterilizing instruments and devices invasive to the human body.

So-called biological indicators are devices that are used to test the efficacy of sterilization processes. Typically, a biological indicator is placed within a sterilization chamber during a sterilization process. The biological indicator system includes a source of microorganisms, a culture medium, and a visible detector to indicate the presence or absence of viable microorganisms. The source of microorganisms is typically an absorbent paper strip that has been impregnated with a pre-determined concentration of viable microorganisms. After the biological indicator has been subjected to the sterilization process, the microorganism-impregnated strip is exposed to the sterile culture medium, and incubated for a predetermined time at an appropriate temperature. At the end of the incubation period, the indicator is evaluated either visually or with a detector to determine whether any microorganisms survived the sterilization process.

The present invention provides a self-contained biological indicator for determining the efficacy of a sterilization process.

SUMMARY OF THE INVENTION

In accordance with a preferred embodiment of the present invention, there is provided a self-contained biological indicator for evaluating the effectiveness of a sterilizer utilizing: an anti-microbial gas or liquid fluid. The indicator is comprised of a tubular casing having open ends and defining an interior chamber. A source of viable microorganisms is disposed within the chamber. A frangible ampoule containing a culture medium capable of promoting growth of the microorganism and a detector means capable of reaction with the metabolites of the microorganism to produce a visual indication is disposed within the chamber. The ampoule is operable by pressure applied to an external surface thereof to permit the microorganism and the medium to come into contact with each other. A cap assembly is mounted to each end of the tubular casing. Each cap assembly includes a telescoping element movable from a first position defining an opening communicating with the chamber and a(,second position forming a gas/fluid impermeable seal around the chamber. The telescoping element includes surface means to engage and crush the ampoule as the telescoping member moves from the first position to the second position.

The biological indicator of the present invention provides an advantage in that spores or microorganisms which may be washed off of a paper strip or other spore-carrying element are captured within the chamber of the device.

Another advantage of the present invention is the provision of a self-contained biological indicator that reduces the potential of operator contamination.

Yet another advantage of the present invention is the provision of a biological indicator that is suitable for use with commercially available gas, steam and liquid sterilization processes.

Yet another advantage in a liquid sterilization system is a biological indicator that may be used in a sterilizer in the presence of a medical device.

A still further advantage of the present invention is a biological indicator as described above that prevents microorganisms in the indicator from contaminating the medical device in a sterilizer during the liquid sterilization cycle.

These and other objects will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
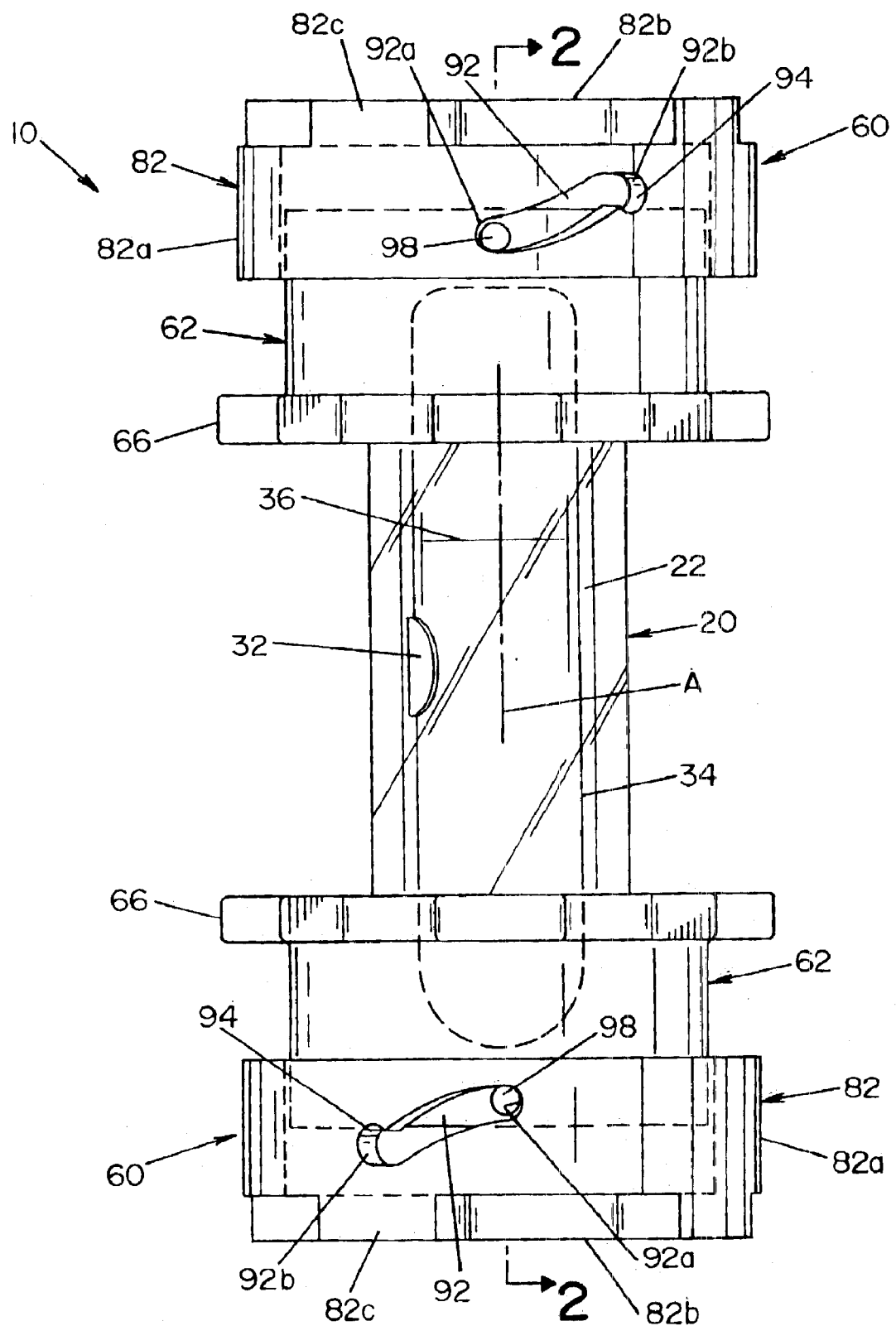
FIG. 1 is a view of a biological indicator assembly, illustrating a preferred embodiment of the present invention.

Referring now to the drawings wherein the showings are for the purpose of illustrating a preferred embodiment of the invention only, and not for the purpose of limiting same, FIG. 1 shows a biological indicator 10 in accordance with a preferred embodiment of the present invention. Broadly stated, biological indicator 10 is comprised of a tubular casing 20 having a cap assembly 60 attached to the ends thereof. Casing 20 is dimensioned to hold a microorganism-inoculated element 32 and an ampoule 34 containing a growth medium 36. Cap assemblies 60 are operable to move between a first configuration, wherein the microorganism-inoculated element 32 is exposed to the environment surrounding biological indicator 10, and a second position wherein the interior of casing 20 is sealed from the surrounding environment.

Figure 2:
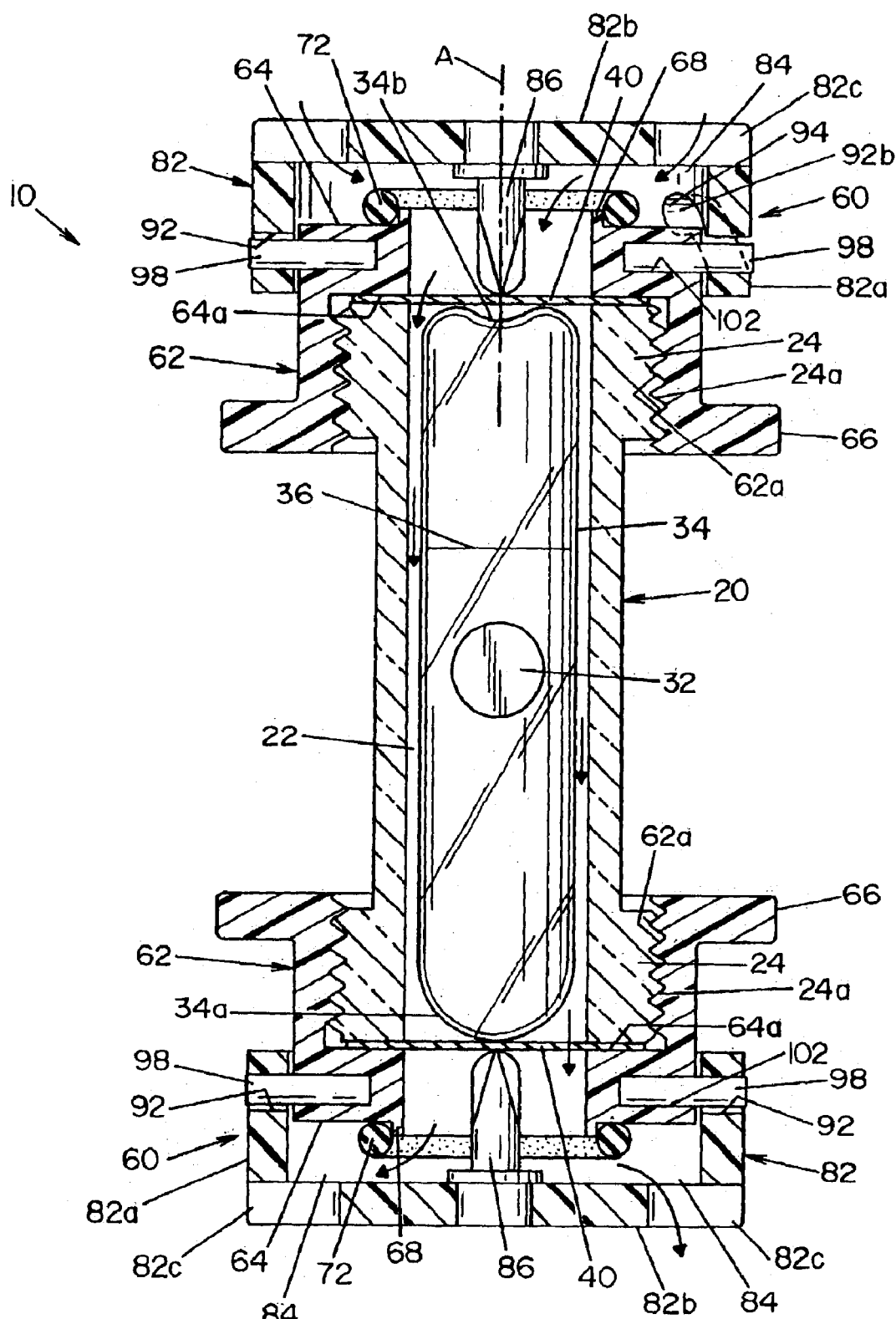
FIG. 2 is a sectional view taken along lines 2—2 of FIG. 1, showing the biological indicator in a first configuration exposing a microorganism-inoculated element to the environment surrounding the biological indicator.

Referring now to FIG. 2, casing 20 is best seen. In the embodiment shown, casing 20 is cylindrical in shape and defines an interior cylindrical cavity 22. Casing 20 is preferably formed of a translucent, polymer material, such as by way of example and not limitation, polypropylene, polyethylene, polycarbonate, polyvinyl carbonate, polyvinyl styrene, polyvinyl acetate, polymethylmethacrylate or any copolymers of the above materials. Casing 20 includes outwardly extending flanges 24 at the distal ends thereof. Flanges 24 include outer surfaces 24a that are formed to have conventional screw threads formed thereon.

Cavity 22 of casing 20 is dimensioned to receive ampoule 34 containing growth-promoting medium 36. Growth-promoting mediums are well known to those skilled in the art, and therefore shall not be described in detail. Examples of suitable growth-promoting mediums that find advantageous application in the present invention are trypic soy broth and soybean casein digest growth media.

In the embodiment shown, ampoule 34 is a sealed enclosure formed from a frangible material, such as glass or other suitable materials, which would allow ampoule 34 to be opened by crushing when an external force of certain pressure is applied thereto, as shall be described in greater detail below. In the embodiment shown, ampoule 34 includes a generally hemispherical end 34a and a dished or concaved end 34b. It shall be appreciated by a further reading of the specification, that ampoule 34 may assume different shapes without departing from the scope of the present invention.

A microorganism-inoculated element 32, such as a paper patch inoculated with spores or other microorganisms, as is conventionally known in the art, is disposed within inner cavity 22 defined by tubular casing 20. Microorganism-inoculated element 32 may be attached to the inner surface of casing 20, but in the embodiment shown is affixed to the outer surface of ampoule 34, as illustrated in the drawings.

A barrier member 40 is disposed at each end of casing 20 to enclose the ends of cavity 22. Barrier member 40 is formed of a material that is fluid permeable, but microorganism impermeable. Barrier member 40 may be formed of cellulose material, a polymeric material, such as polypropylene, polyethylene, polyvinyl-carbonate, polyvinyl styrene, nylon, a mixture of polymeric materials or an advanced materials membrane could be used. In a preferred embodiment of the present invention, barrier member 40 is formed of nylon 6. In the embodiment shown, barrier member 40 is a circular disk or sheet (best seen in FIG. 4). Barrier member 40 is captured between cap assembly 60 and the ends of casing 20.

Figure 4:
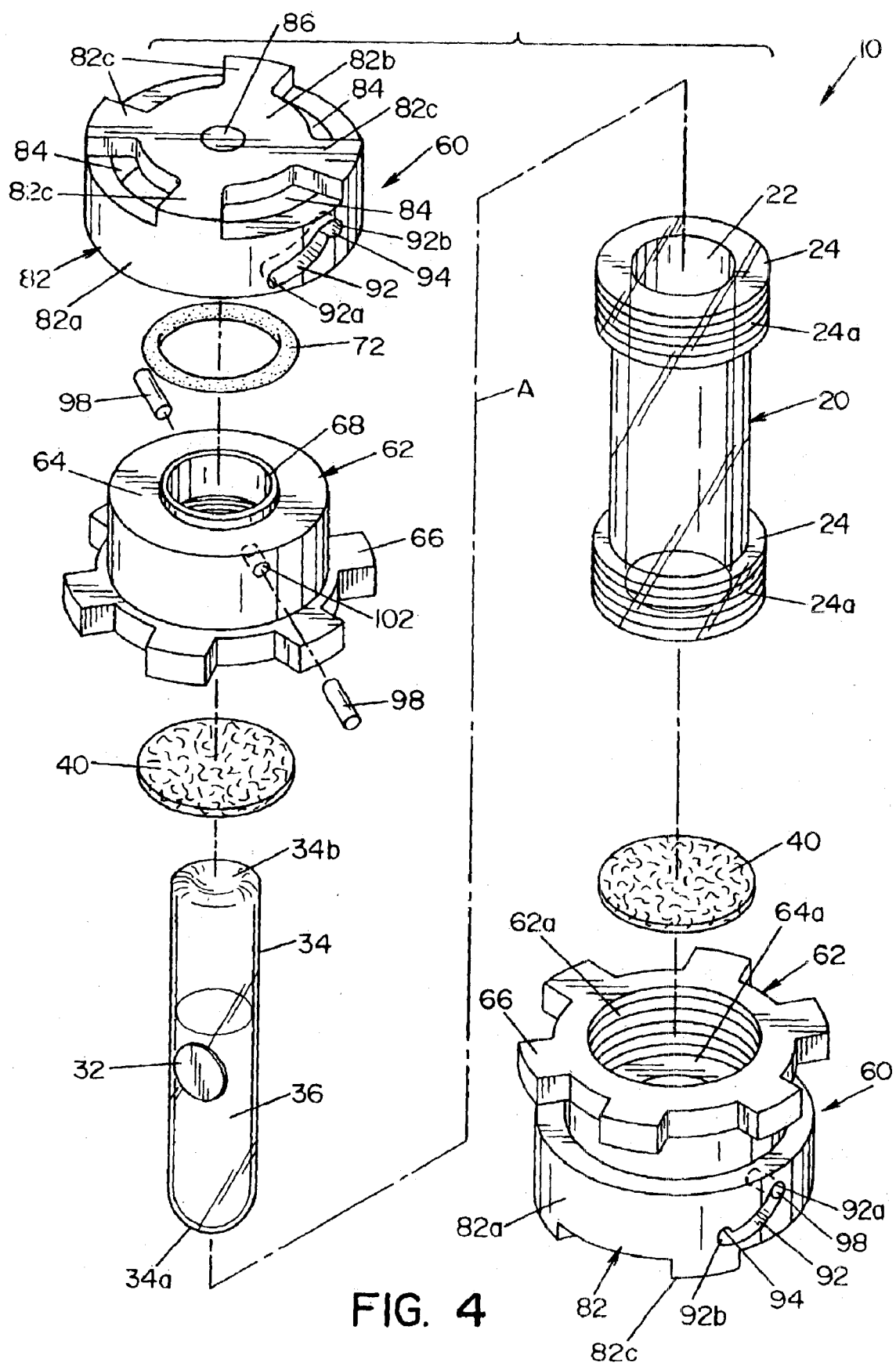
FIG. 4 is an exploded view of the biological indicator shown in FIG. 1.

Each cap assembly 60 is generally comprised of a sleeve 62 and a cap 82 that is moveable relative to the sleeve 62. In the embodiment shown, sleeve 62 is a generally tubular member dimensioned to be screwed onto the end of casing 20. In this respect, sleeve 62 has an internally threaded surface 62a dimensioned to matingly engage threaded surface 24a on flange 24. An inwardly extending, annular wall 64 is formed at one end of sleeve 62. Annular wall 64 includes an annular surface 64a that is operable to capture barrier member 40 against the end of casing 20. The other end of sleeve 62 includes an outwardly extending splined flange 66, as best seen in FIG. 4. Splined flange 66 is provided to facilitate screwing sleeve 62 onto flange 24 of casing 20.

A short annular wall or collar 68 is formed along the edge of annular wall 64. Collar 68 is dimensioned to receive an O-ring 72, as shown in the drawings. As best seen in FIG. 2, O-ring 72 is larger than collar 68 such that a portion of O-ring 72 extends beyond the end of collar 68.

Cap 82 is generally cup-shaped and includes a cylindrical wall portion 82a, and a planar end portion 82b that is joined to cylindrical wall portion 82a by a plurality of radially extending arms 82c (best seen in FIG. 4). Arms 82c define a plurality of openings 84 through to cap 82. In this respect, cap 82 is generally symmetrical about a central axis "A" that extends through casing 20. A spike element 86 extends inwardly from end portion 82 along the central axis of cap 82.

A pair of slots 92, best seen in FIGS. 1 and 4, are formed of a cylindrical wall portion 82a of cap 82. Each slot 92 has a first end 92a and a second end 92b. Slots 92 are formed on opposite sides of a cylindrical wall portion 82a. Each slot 92 is formed at an angle relative to the central axis of cap 82, wherein second end 92b of each slot 92 is closer to end portion 82b than the first end 92a. Second end 92b of each slot 92 is formed to define a detent, or rest area 94, as shall be described in greater detail below.

Cap 82 is attached to sleeve 62 by a pair of pins 98 that extend outwardly from sleeve 62. Pins 98 are aligned with each other and extend from opposite sides of sleeve 62, as best seen in FIGS. 2 and 4. Pins 98 are dimensioned to be received in bores 102 formed in sleeve 62, as best seen in FIG. 4. In this respect, a cap assembly 60 is formed by placing O-ring 72 on collar 68 of sleeve 62, and by then positioning cap 82 over sleeve 62. Pins 98 are then inserted through slots 92 into bores 102 formed within sleeve 62. Each pin 98 is preferably dimensioned to be press-fit into its corresponding bore 102, wherein pins 98 remain in place in sleeve 62 once inserted therein.

The present invention shall now be further described with respect to assembly of indicator 10. A microorganism-inoculated test element 32 is attached to ampoule 34 containing a growth-promoting medium 36. Ampoule 34 with microorganism-inoculated test element 32 thereon is inserted into tubular casing 20. O-rings 72 are then placed over collars 68 at each end of casing 20. A barrier element 40 is positioned over the ends of casing 20. A cap assembly 60, as heretofore described, is then screwed onto each end of casing 20. Specifically, cap assembly 60 is attached to casing 20 by using splined flange 66 on sleeve 62 to screw sleeve 62 onto threaded flange 24 of casing 20. Sleeve 62 is screwed onto casing 20 until annular surface 64a of annular wall 64 forces barrier element 40 into sealing a contact with the surface of flange 24, as best seen in FIG. 2. In this respect, cap assembly 60 is designed such that the tip of spike element 86 just engages, or is in near engagement with, barrier element 40, and cap 82 is disposed relative to sleeve 62 such that pins 98 are disposed at first ends 92a of slots 92. Barrier member 40 when captured between sleeve 62 and casing 20 has sufficient structural integrity to maintain cap 82 spaced from sleeve 62 in the position shown in FIG. 2. As seen in FIG. 2, ampoule 34 is dimensioned such that ends 34a, 34b thereof are near, or in contact with, barrier element 40. In other words, ampoule 34 has a length approximately equal to the length of casing 20.

Referring now to its operation, indicator 10 is placed within a chamber of a sterilizer (not shown) along with objects to be sterilized. Indicator 10 has an initial "open configuration," as illustrated in FIG. 2. During a sterilization cycle, steriliant fluid (gas or liquid) permeates through openings 84 in cap 82, and through barrier element 40 into cavity. 22 of casing 20 where it (the steriliant fluid) acts on the microorganism-inoculated element 32 on ampoule 34.

Figure 3:
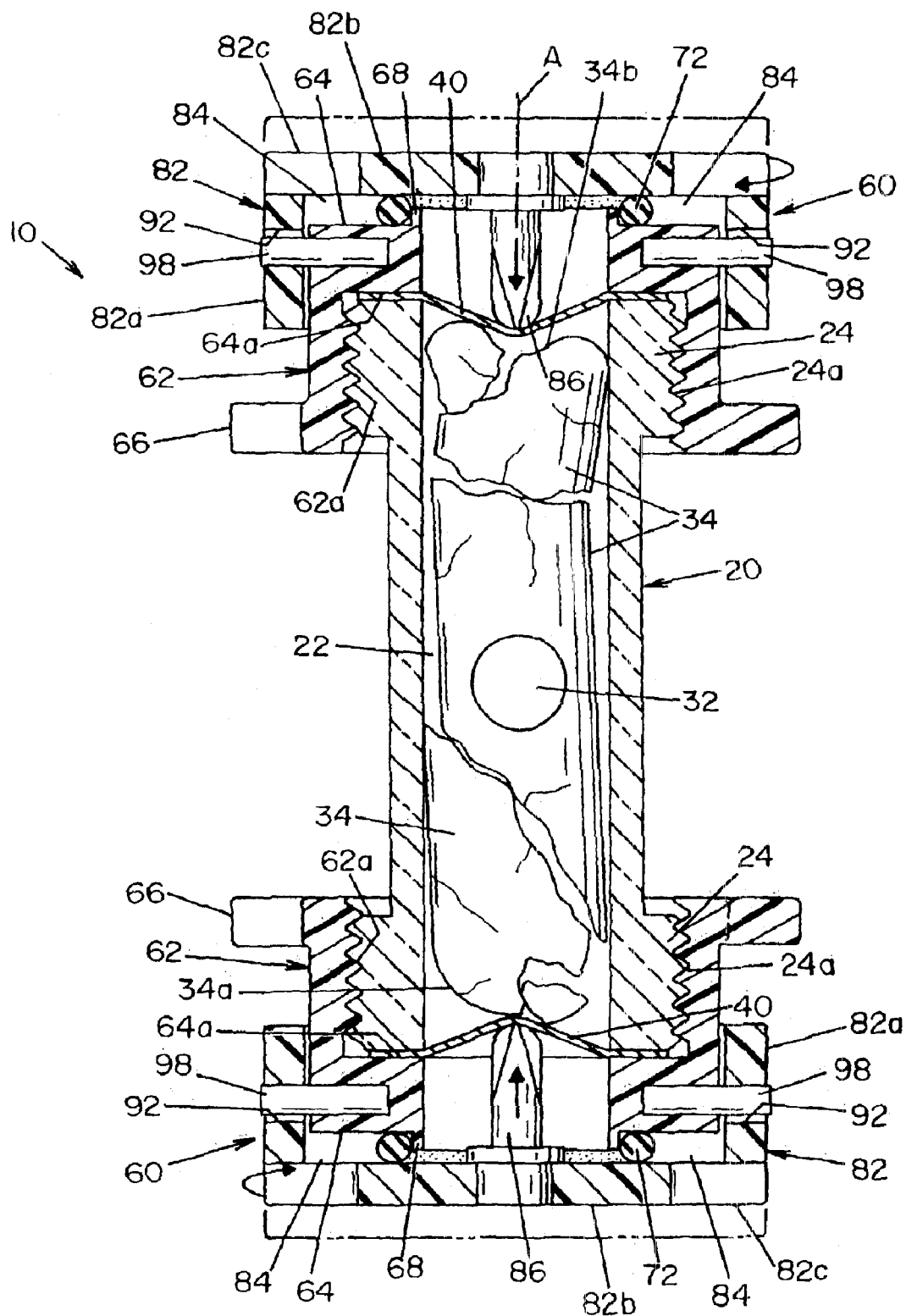
FIG. 3 is a sectional view showing the biological indicator in a second configuration, wherein the microorganism-inoculated element is environmentally sealed within the biological indicator and is exposed to a growth medium.

After being subjected to the sterilization cycle, indicator 10 is removed from the chamber of the sterilizer and is "sealed," by angularly rotating, i.e., twisting, caps 82 relative to sleeve 62 and casing 20. In the embodiment shown, caps 82 are twisted clockwise relative to sleeve 62 and casing 20 about axis "A" therethrough. Such twisting motion causes each cap 82 to be drawn inwardly towards its associated sleeve 62. The twisting of caps 82 about axis "A" basically produces a telescoping action as caps 82 are drawn toward casing 20. FIG. 3 illustrates how cap 82 moves inwardly toward casing 20 from its original "open" position, shown in phantom in FIG. 3, to its "closed" position. The inward, telescoping movement of caps 82 moves spike elements 86 against barrier members 40 and forcing same against ends 34a, 34b of ampoule 34. The localized pressure exerted on ends 34a, 34b of ampoule 34 by spike elements 86 is sufficient to crush the frangible container, thereby exposing the microorganisms on microorganism-inoculated element 32 to growth-promoting medium 36 within ampoule 34. At the same time that spike elements 86 are crushing ampoule 34, tubular casing 20 is being sealed at its ends as end portions 82b of caps 82 are being forced into sealing engagement with O-rings 72. The movement of cap 82 relative to sleeve 62 is the result of pins 98 following, i.e., moving in, slots 92 as caps 82 are being turned relative to sleeves 62. Slots 92 basically act as a cam surface forcing caps 82 to move toward sleeves 62 as pins 98 move through slots 92 from first end 92a to second end 92b thereof As indicated above, slots 92 are essentially straight, but have an over center or rest position or detent position 94 formed at second end 92b thereof Detent positions 94 of slots 92 define "rest positions," wherein pins 98 basically snap into rest positions 94 and thereby lock cap 82 in a sealed position against sleeve 62, as illustrated in FIG. 3. A lip formed at rest position 94 prevents cap 82 from easily reversing direction, and moving away from sleeve 62.

The crushing of ampoule 34 and sealing of casing 20 basically "activates" indicator 10. Once activated, indicator 10 is placed in a conventional incubator (not shown) at a temperature and for a time suitable for growing the microorganism in growth-promoting medium 36.

It is known in the art to utilize a so-called detector contained in growth medium 36, which is capable of undergoing a visual change in color or change in turbidity in response to the growth of a particular microorganism. The metabolites produced by a particular microorganism are designed to react with a given detector to produce a color change or change in turbidity indicating that sterilization was not complete. The absence of a color change or turbidity after a predetermined period of time, confirms that sterilization conditions were achieved.

The present invention thus provides a self-contained biological indicator 10 that is simple to use and is easily self-sealing. Indicator 10 is particularly applicable to a liquid sterilant process, but also finds advantageous application in steam and vapor sterilization processes.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. A self-contained biological indicator for evaluating the effectiveness of a sterilizer utilizing an anti-microbial gas or liquid fluid, said indicator comprising:

a tubular casing having open ends and defining an interior chamber;

a source of viable microorganisms disposed within said chamber;

a frangible ampoule containing a culture medium capable of promoting growth of said microorganism and a detector means capable of reaction with the metabolites of said microorganism to produce a visual indication, said ampoule being disposed within said chamber and being operable by pressure applied to an external surface thereof to permit said microorganism and medium to come into contact with each other;

a cap assembly mounted to each end of said tubular casing, said cap assembly including a telescoping element movable from a first position defining an opening communicating with said chamber and a second position forming a gas/fluid impermeable seal around said chamber, said telescoping element including surface means to engage and crush said ampoule as said telescoping member moves from said first position to said second position and wherein said cap assembly includes a first member mounted to said tubular casing and a second member movably mounted to said first member, wherein said second member is movable on said first member from said first position to said second position.

2. A self-contained biological indicator as defined in claim 1, further comprising a barrier element disposed between said cap assembly and said chamber, said barrier element being impermeable to said microorganisms, but permeable to said gas/liquid anti-microbial fluid.

3. A self-contained biological indicator as defined, in claim 2, wherein said barrier element is comprised of a sheet of membrane or filter material that is captured between said casing in said cap assembly.

4. A self-contained biological indicator as defined in claim 1, wherein said source of microorganisms includes a paper sheet inoculated with a predetermined concentration of said microorganisms.

5. A self-contained biological indicator as defined in claim 4, wherein said paper sheet is attached to an external surface of said ampule.

6. A self-contained biological indicator as defined in claim 5, wherein said telescoping member is angularly and linearly movable relative to an axis through said casing.

7. A self-contained biological indicator as defined in claim 6, wherein said second member is rotatable about said axis, and wherein rotation of said second member about said axis causes said second member to move axially toward said first member.

8. A self-contained biological indicator as defined in claim 7, wherein:

said casing is cylindrical in shape and has threaded end portions;

said first member is a cylindrical sleeve threaded onto said threaded end portion of said cylindrical sleeve; and said second member is a generally cylindrical cap, said cap being mounted to said sleeve on pins extending from said sleeve through slots in said cap.

9. A self-contained biological indicator as defined in claim 8, further comprising an O-ring disposed between said cap and said sleeve that is operable to form a seal between said cap and said sleeve when said cap is in said second position.

10. A self-contained biological indicator as defined in claim 6, wherein said surface means is a punch movable along said axis.

* * * * *

UNITED STATES PATENT AND TRADEMARK OFFICE
CERTIFICATE OF CORRECTION

PATENT NO. : 6,924,139 B2
DATED : August 2, 2005
INVENTOR(S) : Randal W. Eveland et al.

It is certified that error appears in the above-identified patent and that said Letters Patent is hereby corrected as shown below:

<u>Title page,</u>
Item [75], Inventors, should include -- Jeffery R. Horacek, Mentor, OH (US) --.

Signed and Sealed this

Fourth Day of October, 2005

JON W. DUDAS
*Director of the United States Patent and Trademark Office*

UNITED STATES PATENT AND TRADEMARK OFFICE
CERTIFICATE OF CORRECTION

PATENT NO. : 6,924,139 B2
DATED : August 2, 2005
INVENTOR(S) : Randal W. Eveland et al.

It is certified that error appears in the above-identified patent and that said Letters Patent is hereby corrected as shown below:

Title page,
Item [75], Inventors, insert -- Jeffery R. Horacek, Mentor, OH (US) --.

Signed and Sealed this

Twenty-fourth Day of January, 2006

JON W. DUDAS
*Director of the United States Patent and Trademark Office*

UNITED STATES PATENT AND TRADEMARK OFFICE
CERTIFICATE OF CORRECTION

PATENT NO.   : 6,924,139 B2  Page 1 of 1
DATED        : August 2, 2005
INVENTOR(S)  : Randal W. Eveland et al.

It is certified that error appears in the above-identified patent and that said Letters Patent is hereby corrected as shown below:

<u>Title page,</u>
Item [75], Inventors, insert -- Jeffrey R. Horacek, Mentor, OH (US) --.

This certificate supersedes Certificate of Correction issued October 4, 2005 and January 24, 2006.

Signed and Sealed this

Twenty-third Day of May, 2006

JON W. DUDAS
*Director of the United States Patent and Trademark Office*